United States Patent [19]

Eickholt

[11] Patent Number: 4,613,682

[45] Date of Patent: Sep. 23, 1986

[54] ETHER SYNTHESIS

[75] Inventor: Kathryn A. Eickholt, Midland, Mich.

[73] Assignee: The Dow Chemical Company, Midland, Mich.

[21] Appl. No.: 767,222

[22] Filed: Aug. 19, 1985

[51] Int. Cl.$^4$ ............................................. C07C 41/16
[52] U.S. Cl. ..................................... 560/61; 558/423; 568/584; 568/585; 568/586; 568/630; 568/631; 568/644; 568/648; 568/636
[58] Field of Search ............... 568/630, 790, 648, 631, 568/644, 636, 584, 585, 586; 560/61; 558/423

[56] References Cited

U.S. PATENT DOCUMENTS 4,349,487  9/1982  Renga et al. ................... 568/630 X

FOREIGN PATENT DOCUMENTS 276014  10/1970  U.S.S.R. .

OTHER PUBLICATIONS

Morrison, R. T. et al., *Organic Chemistry*, 3rd Ed., p. 556 (1975).
Royal Soc. of London, *Catalysis*, vol. 4, Chap. 1 (1981).
Gurudutt, Tetrahedron, 38(12), p. 1843 (1982).

*Primary Examiner*—Bernard Helfin

[57] ABSTRACT

The vapor phase reaction of phenolic compounds with organic halides to form aromatic ethers is catalyzed by metal oxides. The halide value of the organic halide is retained as hydrogen halide which can be reacted with a halide acceptor such as methanol to form methyl halide and water.

20 Claims, No Drawings

4,613,682

ETHER SYNTHESIS

BACKGROUND OF THE INVENTION

This invention relates to processes for producing aromatic ethers. It more specifically relates to the vapor phase production of aromatic ethers from phenols. Aromatic ethers are useful reactants and solvents, heat-transfer media and herbicides.

Williamson's ether synthesis is a well-known process for the manufacture of ethers. Williamson's ether synthesis can be the liquid phase reaction of a sodium phenoxide and an alkyl halide to form an alkyl, phenyl ether and sodium halide salt. See Morrison, R. T., et al., *Organic Chemistry*, 3rd ed, p. 556 (1975). This process disadvantageously consumes stoichiometric amounts of NaOH (to generate the sodium phenoxide) and disadvantageously produces a stoichiometric amount of a sodium halide salt by-product (which converts the high value halide reactant to a low value product).

Alternate processes which do not form unacceptable by-products are also known. Direct alkylation of phenols by treatment with diazomethane, tetramethoxymethane or pentamethoxyphosphorane, have been previously disclosed in the art. Other processes involve treating phenol with methanol in the presence of dicyclohexylcarbodiimide or a mixture of diethylazodicarboxylate and triphenylphosphine. These processes have proven to be rather inefficient, uneconomical or ecologically unsuitable.

Soviet Pat. No. 276,014, issued to I. I. Yukel'son et al. teaches that a catalyst containing the mixture of 45–55 percent $Cr_2O_3$, 25–30 percent $Fe_2O_3$ and 20–25 percent ZnO catalyzes the liquid phase alkylation of phenol and t-butyl chloride to alkyl phenols at over 98 percent yield. Most of the product is dialkylated. This reaction does not produce ethers.

It would be desirable to have a process that converted aromatic alcohols to ethers without consuming a stoichiometric amount of a catalyst and without generating a stoichiometric amount of a halide salt.

SUMMARY OF THE INVENTION

The present invention is such a process for producing aromatic ethers. This process comprises contacting a phenolic compound, in the vapor phase, and an organic halide (which has a haloaliphatic moiety), in the vapor phase with a catalytic amount of a solid catalyst containing a metal oxide or a metal under conditions such that the corresponding ether and hydrogen halide are formed.

It is surprising that an ether is formed, particularly in view of Soviet Pat. No. 276,014 which teaches alkylation instead of the etherification observed in the process of this invention.

This process produces ethers without consuming a stoichiometric amount of a catalyst. It further does not produce stoichiometric amounts of a salt. The process produces a hydrogen halide as a by-product which is of more utility and value than are the by-products produced by previous processes.

DETAILED DESCRIPTION OF ILLUSTRATIVE EMBODIMENTS

The phenolic compounds for use in the invented process are compounds of formula $Ar(OH)_x$, where Ar is any aromatic carbocyclic group, unsubstituted or substituted with one or more groups, which are unreactive under the reaction conditions, and x is an integer from 1 up to and including the number corresponding to total available substitution for Ar, preferably x is 1 or 2.

In the above formula, a monovalent Ar can be phenyl, naphthyl, biphenylyl, or the similar monovalent aromatic moieties which are optionally substituted with unreactive groups. Such unreactive groups may be either electron-donating or electron-withdrawing substituents and include lower alkyl, lower alkoxy, halo, cyano, nitro, ester groups, trifluoromethyl, aralkyl and phenoxy. If x is greater than one, Ar represents the multivalent aromatic moieties, e.g., phenylene, biphenylene, naphthylylene, alkylidene diphenylene, alkylene triphenylene, oxydiphenylene, and similar aromatic diyls, aromatic triyls and aromatic polyyls, etc., which are also optionally substituted as described above.

Preferably, the phenolic compound is phenol itself or a phenol substituted with one or more unreactive groups. Most preferably, the phenolic compound is phenol itself.

The organic halides suitable for the purposes of this invention are those wherein at least one of the halo atoms is bound to an aliphatic carbon and is capable of undergoing reaction with a phenolic moiety to form an ether. Preferable organic halides are compounds of up to about 20 carbons of the formula $RX_n$ where X is chloro, bromo or iodo, provided that X is bound to an aliphatic carbon atom; n is one or two. If n is one, R is alkyl, aralkyl or an alkyl or aralkyl group further substituted with alkoxy, alkoxy(polyalkyleneoxy), aryloxy, cyano, nitro or ester groups. If n is 2, R is the corresponding alkylene, aralkylene group or such group further substituted with alkoxy, alkoxy(poly)alkyleneoxy, aryloxy, cyano, nitro or ester groups as above described. Most preferred are those compounds wherein n is 1 and X is chloro.

Examples of these organic halides include: chloroethane, 1-bromohexane, 1-chlorododecane, chloroacetonitrile, 1-chloro-2-methoxyethane, chloromethoxyethoxymethane, 1-chloro-3-nitropropane, methyl chloromethylacetate, ethyl chloromethylacetate, phenyl chloromethylacetate, benzyl chloride, benzyl bromide, 1-chloro-2-phenoxypropane, 2-chloro-2-methylpropane, 2-chloropropane, β-chlorovinylbenzene and the like.

Suitable catalysts are solid materials containing a metal oxide or metal which cause the reaction of the phenols and a suitable organic halide to form hydrogen halides and corresponding aromatic ethers. Preferred are transition metals and their oxides, rare earth oxides, silica and carbon catalysts which are optionally supported. Most preferred are catalysts selected from the group of: Pd supported on $Al_2O_3$, ZnO, $Al_2O_3$, $TiO_2$ and $Y_2O_3$. These catalysts are commercially available. The supported catalysts can be prepared by standard impregnation methods such as those set forth in chapter 1 of the fourth volume of *Catalysis* published by the Royal Society of Chemistry in London (1981). The surface area of the catalysts is not critical, but typically ranges from about 10 m²/g to about 250 m²/g, preferably from about 100 m²/g to about 250 m²/g.

The reaction can be carried out at any operable temperature and pressure. Preferred is atmospheric pressure. Preferably, reaction temperatures are below about 400° C., more preferably below about 300° C. and most preferably below about 270° C. Preferably, reaction temperatures are above about 100° C., more preferably above about 150° C., even more preferably above about 200° C. and most preferably above about 230° C.

The reaction can occur in any container which can contain the reaction mixture and allow the reaction to proceed. Preferred are normal stainless steel reactors.

The reactants are preferably mixed together, pumped into a heated inert carrier gas stream which vaporizes the reactants and carries them to the catalyst where they can react. The heated inert carrier gas can be any operable non-reactive gas. Examples include nitrogen, argon, and other inert gases.

The reactants can be combined in any operable ratio. Preferably, the more expensive reactant is exceeded by the less expensive reactant by less than about 2:1, more preferably less than about 1.5:1, most preferably less than about 1.2:1.

Preferably, the selectivity is greater than about 50 percent, more preferably more than about 75 percent, most preferably more than about 80 percent. In especially preferred embodiments, the selectivity is more than about 90 percent. Selectivity is defined, for the purposes of this patent, as the amount of the reacted phenolic compound which is converted into the ether product.

The reactants in gaseous state are passed over or through the catalyst at a rate sufficient to achieve the desired conversion of reactants and yield of products with minimum formation of undesired by-products. A continuous flow of reactants is preferably employed wherein the reactants are in contact with the catalyst for uniform periods of time, i.e., no part of the reactants remain in contact with catalyst for prolonged periods of time.

The reactants are thus in contact with the catalyst for a sufficient time for the reaction to proceed, preferably to at least about 50 percent completion, more preferably to at least about 75 percent completion. A typical residence time of reactants in the reactor is between about 20 seconds and about 30 seconds. Flow rates of from about 10 standard cubic centimeters per minute (scc/m) through about 200 scc/m are preferred, more preferred are those between about 30 scc/m and about 70 scc/m.

The reaction produces hydrogen halide as one of the reaction products. The hydrogen halide can be reacted as generated with a halogen acceptor. Suitable halogen acceptors are those that react with the generated hydrogen halide and do not prevent the reaction from proceeding. Preferred halogen acceptors are alcohols in which the hydroxy moiety is bound to an aliphatic carbon atom, tertiary amines and dialkyl carbonates. Most preferred are methanol and diethyl carbonate.

The invention is further illustrated and not limited by the following illustrative embodiments in which unspecified percentages are weight percentages.

ILLUSTRATIVE EMBODIMENT 1

A 20-ml portion of .24 percent ZnO on $\alpha\text{-Al}_2\text{O}_3$ is placed in a stainless steel tube (0.25-inch inside diameter, 12-inch length) and heated by a nitrogen gas stream. A mixture of 36 g of phenol, 30 g of methanol and 6 g of toluene (as a gas chromatograph standard) is passed over the prepared catalyst at a rate of 5 grams/hour as the temperature is raised from 116° C. to 203° C. The products are periodically sampled by a gas chromatograph. No products are detected.

To the 33 g of mixture remaining from Illustrative Embodiment 1 is added 4 g of methyl chloride. This new mixture is passed over the same catalyst at a rate of 5 grams/hour while the temperature is raised from 90° C. to 255° C. Periodic gas chromatograph analysis shows anisole formation over the tested temperature range.

ILLUSTRATIVE EMBODIMENT 2

Illustrative Embodiment 1 is repeated with a mixture of 32 g of phenol, 56 g of methyl chloroacetate, 13 g of methanol and 8 g of dimethoxy benzene (as a gas chromatograph standard). Methyl phenoxy acetate is formed.

ILLUSTRATIVE EMBODIMENT 3

Illustrative Embodiment 2 is repeated using $TiO_2$ pellets as the catalyst. At a temperature of 230° C., the selectivity to methyl phenoxy acetate based on phenol is 100 percent while the conversion of phenol is 3 percent.

ILLUSTRATIVE EMBODIMENT 4

Illustrative Embodiment 1 is repeated with a feed mixture of 94 g of methyl chloroacetate, 68 g of phenol and 5 g of dimethoxybenzene (as a gas chromatograph standard). A catalyst of 22 percent $Y_2O_3$ on $\alpha\text{-Al}_2\text{O}_3$ produces methyl phenoxy acetate.

ILLUSTRATIVE EMBODIMENT 5

Illustrative Embodiment 4 is repeated with a $\gamma\text{-Al}_2\text{O}_3$ catalyst. At a temperature of 230° C., the phenol conversion is 7 percent and the selectivity is 84 percent to methyl phenoxy acetate. Phenyl chloroacetate and transesterification between phenol and dimethoxybenzene are observed.

Illustrative Embodiments 1-5 illustrate the formation of ethers with a variety of reactants.

What is claimed is:

1. A process of making aromatic ethers comprising the step of contacting, in the vapor phase, a phenolic compound and an organic halide (which has a haloaliphatic moiety), with a catalytic amount of a solid catalyst containing a metal oxide or a metal under conditions such that the corresponding ether and hydrogen halide are formed.

2. The process of claim 1 in which the hydrogen halide is reacted with a halide acceptor as the hydrogen halide is generated.

3. The process of claim 1 in which the phenolic compound is of the formula $Ar(OH)_x$, where Ar is any aromatic carbocyclic, unsubstituted or substituted with one or more groups, which are unreactive under the reaction conditions, and x is an integer from 1 up to and including the number corresponding to the total available substitution for Ar.

4. The process of claim 2 in which the phenolic compound is of the formula $Ar(OH)_x$, where Ar is any aromatic carbocyclic, unsubstituted or substituted with one or more groups, which are unreactive under the reaction conditions, and x is an integer from 1 up to and including the number corresponding to the total available substitution for Ar.

5. The process of claim 3 in which the phenolic compound is phenol itself or a phenol substituted with an unreactive group.

6. The process of claim 4 in which the phenolic compound is phenol itself or a phenol substituted with an unreactive group.

7. The process of claim 5 in which the phenolic compound is phenol itself.

8. The process of claim 6 in which the phenolic compound is phenol itself.

9. The process of claim 1 in which the organic halide is a compound of up to about 20 carbons of the formula $RX_n$ where X is chloro, bromo or iodo, provided that X is not bound to a carbon atom contained in a benzene ring structure; n is one or two and when n is one, R is alkyl, aralkyl or an alkyl or aralkyl group further substituted with alkoxy, alkoxy(poly)alkyleneoxy, aryloxy, cyano, nitro or ester groups, and when n is two, R is the corresponding alkylene, aralkylene group or such group further substituted with alkoxy, alkoxy(poly)alkyleneoxy, aryloxy, cyano, nitro or ester groups as above described.

10. The process of claim 9 in which n is two.

11. The process of claim 9 in which n is one.

12. The process of claim 1 in which the catalyst is selected from the group of catalysts consisting of transition metals and their oxides, rare earth oxides, silica and carbon catalysts.

13. The process of claim 12 in which the catalyst is selected from the group of catalysts consisting of ZnO, $Al_2O_3$, $TiO_2$, $Y_2O_3$, and Pd on $Al_2O_3$.

14. The process of claim 13 in which the catalyst has a surface area between about 30 $m_2/g$ through about 70 $m^2/g$.

15. The process of claim 1 in which the reaction ocurs at a temperature between about 100° C. and about 400° C.

16. The process of claim 15 in which the reaction occurs at a temperature between about 230° C. and about 270° C.

17. The process of claim 1 in which the selectivity based on the phenolic compound is at least about 75 percent.

18. The process of claim 17 in which the selectivity based on the phenolic compound is at least about 80 percent.

19. A process of making aromatic ethers comprising the step of contacting, in the vapor phase, a phenolic compound and an organic halide selected from the group consisting of methyl chloroacetate and methyl chloride with a catalytic amount of a solid catalyst containing a metal oxide or a metal under conditions such that the corresponding ether and hydrogen chloride are formed.

20. A process of making methyl phenoxyacetate comprising the step of contacting, in the vapor phase, phenol and methyl chloroacetate with a catalytic amount of a solid catalyst containing a metal oxide or a metal under conditions such that methyl phenoxyacetate and hydrogen chloride are formed; wherein the hydrogen chloride, as generated, is reacted with a halide acceptor.

* * * * *